United States Patent
Kanno

(10) Patent No.: US 8,962,871 B2
(45) Date of Patent: Feb. 24, 2015

(54) METHOD FOR PRODUCING 4-BENZYL-1-METHYL-6-OXABICYCLO[3,2,0]HEPTANE DERIVATIVE

(71) Applicant: Kureha Corporation, Tokyo (JP)

(72) Inventor: Hisashi Kanno, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 14/357,085

(22) PCT Filed: Nov. 5, 2012

(86) PCT No.: PCT/JP2012/078659
§ 371 (c)(1),
(2) Date: May 8, 2014

(87) PCT Pub. No.: WO2013/069615
PCT Pub. Date: May 16, 2013

(65) Prior Publication Data
US 2014/0296535 A1    Oct. 2, 2014

(30) Foreign Application Priority Data

Nov. 11, 2011 (JP) .................................. 2011-247994

(51) Int. Cl.
*C07D 305/14* (2006.01)
*C07D 405/06* (2006.01)
(52) U.S. Cl.
CPC .................................... *C07D 405/06* (2013.01)
USPC ........................................................ 549/510

(58) Field of Classification Search
USPC .......................................................... 549/510
See application file for complete search history.

(56) References Cited

U.S. PATENT DOCUMENTS 8,710,090 B2   4/2014 Araki et al.
2012/0232286 A1*  9/2012 Araki et al. ................. 548/267.4

OTHER PUBLICATIONS

English translation of International Preliminary Report on Patentability and Written Opinion issued May 22, 2014, in PCT International Application No. PCT/JP2012/078659.
Nobuyuki Matsunaga et al., "C17,20-lyase inhibitors. Part 2: Design, synthesis and structure-activity relationships of (2-naphthylmethyl)-1H-imidazoles as novel C17,20-lyase inhibitors" Bioorganic & Medical Chemistry, 2004, 4313-4336, vol. 12 (16).
International Search Report of PCT/JP2012/081903 dated Mar. 5, 2013.

* cited by examiner

*Primary Examiner* — Rebecca Anderson
*Assistant Examiner* — Karen Cheng
(74) *Attorney, Agent, or Firm* — Birch, Stewart, Kolasch & Birch, LLP

(57) ABSTRACT

A 4-benzyl-1-methyl-6-oxabicyclo[3,2,0]heptane derivative is manufactured by reducing, in the presence of both a halogenating agent and a hydride-type reducing agent, a methylene moiety bound to a sulfonyloxy group in a compound represented by General Formula (II).

8 Claims, No Drawings

METHOD FOR PRODUCING 4-BENZYL-1-METHYL-6-OXA-BICYCLO[3,2,0]HEPTANE DERIVATIVE

TECHNICAL FIELD

The present invention relates to a novel method for manufacturing 4-benzyl-1-methyl-6-oxabicyclo[3,2,0]heptane derivatives used as an intermediate in agrochemicals.

BACKGROUND ART

Patent Document 1 describes a 2-(halogenated hydrocarbon-substituted)-5-benzyl-1-azolylmethylcyclopentanol derivative which is a compound that can be used as an active ingredient in agricultural and horticultural agents and in industrial material protecting agents. A method is described in the same document, as a step in the method for manufacturing this derivative, in which a 4-benzyl-1-methyl-6-oxabicyclo[3,2,0]heptane derivative (intermediate compound) is obtained by oxetane-cyclizing and sulfonic acid-esterifying a 2,2-bis(hydroxymethyl)cyclopentanol derivative, and then reducing the resulting sulfonic acid-esterified oxetane derivative.

PRIOR ART DOCUMENTS

Patent Documents

Patent Document 1

International Publication WO2011/070771 (Published Jun. 16, 2011).

SUMMARY OF THE INVENTION

Problem Solved by the Invention

However, in order to mass-produce a 2-(halogenated hydrocarbon-substituted)-5-benzyl-1-azolylmethylcyclopentanol derivative inexpensively, the yield of the step in which the sulfonic acid-esterified oxetane derivative is reduced to obtain the 4-benzyl-1-methyl-6-oxabicyclo[3,2,0] heptane derivative has to be improved.

In view of these problems, it is an object of the present invention to provide a method for manufacturing a higher yield of the 4-benzyl-1-methyl-6-oxabicyclo[3,2,0]heptane derivative serving as an intermediate compound.

Means of Solving the Problem

The present inventor conducted extensive research to solve these problems. As a result, he discovered that the yield of 4-benzyl-1-methyl-6-oxabicyclo[3,2,0]heptane derivative could be improved significantly by reducing the sulfonic acid-esterified oxetane derivative in the presence of both a halogenating agent and a hydride-type reducing agent. The present invention is a product of this discovery.

The present invention is a method for the manufacture of a compound represented by General Formula (I) below.

Formula 1

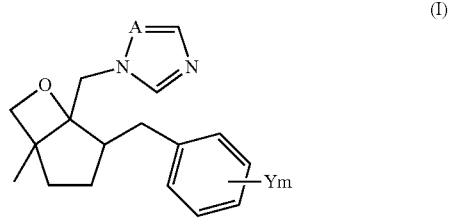

(I)

(In General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group, m represents an integer from 0 to 5, Y being the same or different when m is an integer equal to or greater than 2, and A represents a nitrogen atom or a methine group.)

In this manufacturing method, a compound represented by General Formula (II) below is reduced in the presence of both a halogenating agent and a hydride-type reducing agent.

Formula 1

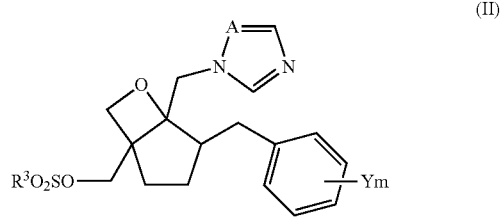

(II)

(In General Formula (II), Y, m and A are the same as Y, m and A in General Formula (I), respectively, $R^3$ represents an alkyl group having 1 to 3 carbon atoms, a haloalkyl group having 1 to 3 carbon atoms, a substitutable phenyl group, or a substitutable naphthyl group.)

Effect of the Invention

The present invention has the effect of being able to manufacture a higher yield of a 4-benzyl-1-methyl-6-oxabicyclo [3,2,0]heptane derivative.

BEST MODE FOR CARRYING OUT THE INVENTION

The following is an explanation of the method for manufacturing a 4-benzyl-1-methyl-6-oxabicyclo[3,2,0]heptane derivative according to the present invention.

SUMMARY OF THE MANUFACTURING METHOD

The manufacturing method according to the present invention is a method for the manufacture of a compound represented by General Formula (I) below.

Formula 3

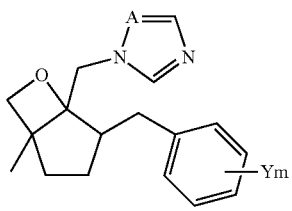
(I)

In this manufacturing method, a compound represented by General Formula (II) below is reduced in the presence of both a halogenating agent and a hydride-type reducing agent.

Formula 4

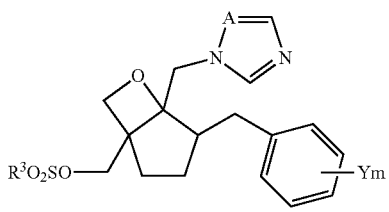
(II)

The following is a more detailed explanation of the compound related to this manufacturing method and to the manufacturing method itself.

Compound Represented by General Formula I

The compound represented by General Formula (I) (referred to as Compound (I) below) is a 4-benzyl-1-methyl-6-oxabicyclo[3,2,0]heptane derivative. This compound can be used advantageously as an active ingredient in agricultural and horticultural agents and in industrial material protecting agents by mixing the compound with a halogen acid in a solvent and opening the oxetane ring (see Patent Document 1).

In General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group.

Examples of halogen atoms represented by Y include fluorine atoms, chlorine atoms, bromine atoms, and iodine atoms. Among these, fluorine atoms, chlorine atoms and bromine atoms are preferred, and chlorine atoms are more preferred.

Specific examples of alkyl groups having 1 to 4 carbon atoms that are represented by Y include a methyl group, ethyl group, n-propyl group, isopropyl group, n-butyl group, isobutyl group, sec-butyl group and tert-butyl group. Among these an alkyl group having 1 to 3 carbon atoms is preferred, an alkyl group having 1 to 2 carbon atoms is more preferred, and a methyl group is even more preferred.

A haloalkyl group having 1 to 4 carbon atoms represented by Y is an alkyl group substituted by a halogen atom or two or more halogen atoms that are the same or different. Examples include a dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, dibromomethyl group, tribromomethyl group, 2-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, diiodomethyl group, 2,2-diiodoethyl group, 1,2-diiodoethyl group, 2,2,2-triiodoethyl group, 2,3-diiodopropyl group, 1-iodo-1-methylethyl group, and 2-iodo-1-methylethyl group. Among these, a haloalkyl group having 1 to 3 carbon atoms is preferred, a haloalkyl group having 1 to 2 carbon atoms is more preferred, and a trihaloalkyl group having 1 carbon atom is even more preferred.

Specific examples of alkoxy groups having 1 to 4 carbon atoms that are represented by Y include a methoxy group, ethoxy group, and n-propoxy group. Among these, an alkoxy group having 1 to 3 carbon atoms is preferred, an alkoxy group having 1 to 2 carbon atoms is more preferred, and a methoxy group is even more preferred.

A haloalkoxy group having 1 to 4 carbon atoms represented by Y is an alkoxy group substituted by a halogen atom or two or more halogen atoms that are the same or different. Examples include a trifluoromethoxy group, difluoromethoxy group, 1,1,2,2,2-pentafluoroethoxy group and 2,2,2-trifluoroethoxy group. Among these, a haloalkoxy group having 1 to 3 carbon atoms is preferred, a haloalkoxy group having 1 to 2 carbon atoms is more preferred, and dihalomethoxy group or trihalomethoxy group having 1 carbon atom is even more preferred.

As defined above, Y is preferably a halogen atom, methyl group, trifluoromethyl group, trifluoromethoxy group, or difluoromethoxy group. Among these, a halogen atom is more preferred, and a chlorine atom is especially preferred.

In General Formula (I), m represents an integer from 0 to 5. Here, m is preferably an integer from 0 to 3, more preferably and integer from 0 to 2, and even more preferably 0 or 1. When m is an integer that is equal to or greater than 2, Y may be the same or different. When m is an integer that is equal to or greater than 1, Y may be located anywhere from the 2- to the 6-position of the benzene ring.

In General Formula (I), A is a nitrogen atom or methine group, and preferably a nitrogen atom.

In Compound (I), m is preferably an integer from 0 to 3 in General Formula (I). When m is an integer that is equal to or greater than 1, Y preferably represents a halogen atom, an alkyl group having 1 to 3 carbon atoms, a haloalkyl group having 1 to 3 carbon atoms, an alkoxy group having 1 to 3 carbon atoms, or a haloalkoxy group having 1 to 3 carbon atoms, and A preferably represents a nitrogen atom. In Compound (I), m is more preferably an integer from 0 to 2 in General Formula (I). When m is an integer equal to or greater than 1, Y preferably represents a halogen atom, and A preferably represents a nitrogen atom.

Compound Represented by General Formula (II)

A compound represented by General Formula (II) above (referred to as Compound (II) below) has a methylene moiety bound to a sulfonyloxy group that is reduced in the reducing reaction described in detail below to obtain Compound (I). Therefore, Y, m and A in General Formula (II) are the same as Y, m and A in General Formula (I), respectively.

In General Formula (II), $R^3$ represents an alkyl group having 1 to 3 carbon atoms, a haloalkyl group having 1 to 3 carbon atoms, a substitutable phenyl group, or a substitutable naphthyl group.

Specific examples of alkyl groups having 1 to 3 carbon atoms that are represented by $R^3$ include a methyl group, ethyl group, n-propyl group and isopropyl group. Among these, a methyl group is preferred.

A haloalkyl group having 1 to 3 carbon atoms represented by $R^3$ is an alkyl group substituted by a halogen atom or by two or more halogen atoms that are the same or different. Examples of halogen atoms represented by Y include fluorine atoms, chlorine atoms, bromine atoms, and iodine atoms. Among these, fluorine atoms or chlorine atoms are preferred. An example of a haloalkyl group having 1 to 3 carbon atoms represented by $R^3$ is a trifluoromethyl group.

A hydrogen atom in a phenyl group or naphthyl group represented by $R^3$ may be substituted by a halogen atom, a methyl group, trifluoromethyl group, nitro group or amino group. Substitutable halogen atoms include fluorine atoms, chlorine atoms, bromine atoms, and iodine atoms. There are no particular restrictions on the number and location of substitutions. Examples of hydrogen atom-substituted phenyl groups include a 4-methyl-phenyl group, 2-methyl phenyl group, and 4-chlorophenyl group. Among these, a 4-methyl-phenyl group is preferred.

$R^3$ is preferably a methyl group or 4-methyl-phenyl group.

There are no particular restrictions on the sulfonyloxy group ($-OSO_2R^3$) as long as it satisfies the definition. Examples include a methanesulfonyloxy group, ethanesulfonyloxy group, propanesulfonyloxy group, trifluoromethanesulfonyloxy group, benzenesulfonyloxy group, 4-chlorobenzenesulfonyloxy group, p-toluenesulfonyloxy group, naphthalene-sulfonyloxy group, and dimethylaminonaphthylsulfonyloxy group. Among these, a methanesulfonyloxy group and a p-toluenesulfonyloxy group are preferred, and a p-toluenesulfonyloxy group is especially preferred from the standpoint of achieving a good reduction reaction in the presence of both a halogenating agent and a hydride-type reducing agent.

Compound (II) can be manufactured by simultaneously producing an oxetane from and sulfonylating a compound represented by General Formula (IV) in the presence of a sulfonyl chloride and base in a solvent (see Patent Document 1). This method is especially preferred when the sulfonyloxy group in Compound (II) is a p-toluenesulfonyloxy group.

Formula 5

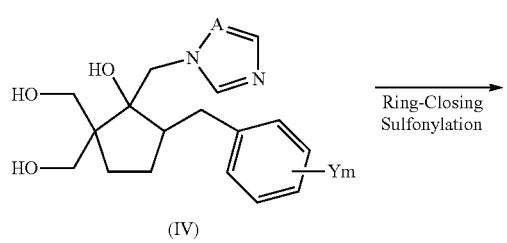

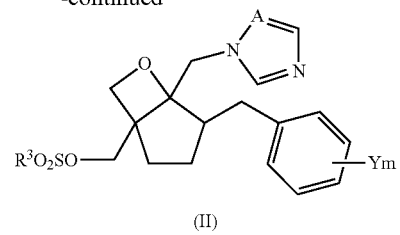

(II)

In General Formula (IV), Y, m and A are the same as Y, m and A in General Formula (I), respectively.

Compound (II) can also be manufactured by bissulfonylating a compound represented by General Formula (IV) in the presence of a sulfonyl chloride and preferably a base in a solvent, and then reacting the product with a base in the solvent and producing an oxetane (see Patent Document 1). This method is especially preferred when the sulfonyloxy group in Compound (II) is a methanesulfonyloxy group.

Formula 6

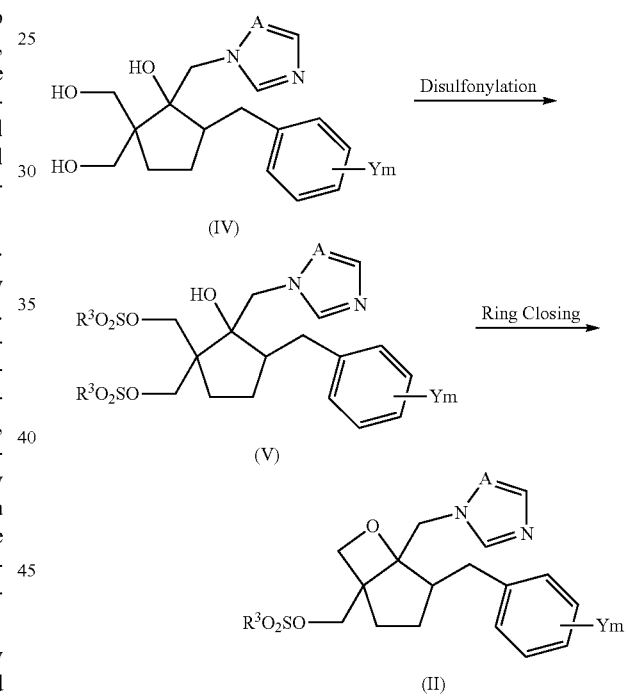

In General Formulas (IV) and (V), Y, m and A are the same as Y, m and A in General Formula (I), respectively. In General Formula (V), $R^3$ is the same as $R^3$ in General Formula (II).

Halogenating Agent

The halogenating agent used in the manufacturing method of the present invention is able to halogenate a sulfonyloxy group in Compound (II). Examples of halogenating agents include alkali metal halides such as sodium iodide, potassium iodide, lithium iodide, sodium bromide, potassium bromide, and lithium bromide. Among these, sodium iodide, potassium iodide and lithium iodide are preferred, and sodium iodide and lithium iodide are especially preferred.

Hydride-Type Reducing Agents

Hydride-type reducing agents used in the manufacturing method of the present invention include borohydride compounds such as diborane, sodium borohydride, lithium borohydride, sodium trimethoxyborohydride, sodium cyanoborohydride, lithium triethylborohydride, potassium borohydride, zinc borohydride, sodium acetoxyborohydride and borane-tetrahydrofuran complexes, as well as aluminum hydride compounds such as lithium aluminum hydride, sodium bis(2-methoxyethoxy)aluminum hydride, sodium aluminum hydride, and diisobutylaluminum hydride. Among these, sodium borohydride, lithium borohydride, sodium trimethoxyborohydride, lithium aluminum hydride, and sodium bis(2-methoxyethoxy)aluminum hydride are preferred. Sodium borohydride is especially preferred.

In a preferred combination of a halogenating agent and a hydride-type reducing agent, the halogenating agent is either sodium iodide or potassium iodide, and the hydride-type reducing agent is sodium borohydride.

Details of Manufacturing Method

In the manufacturing method of the present invention, a methylene moiety bound to a sulfonyloxy group in Compound (II) is reduced in the presence of both a halogenating agent and a hydride-type reducing agent. In the series of reactions represented in Reaction Scheme (1) shown below, it is presumed that the sulfonyloxy group in Compound (II) is substituted with a halogen atom by the halogenating agent, and reduced by the hydride-type reducing agent.

Reaction Scheme (1)

Formula 7

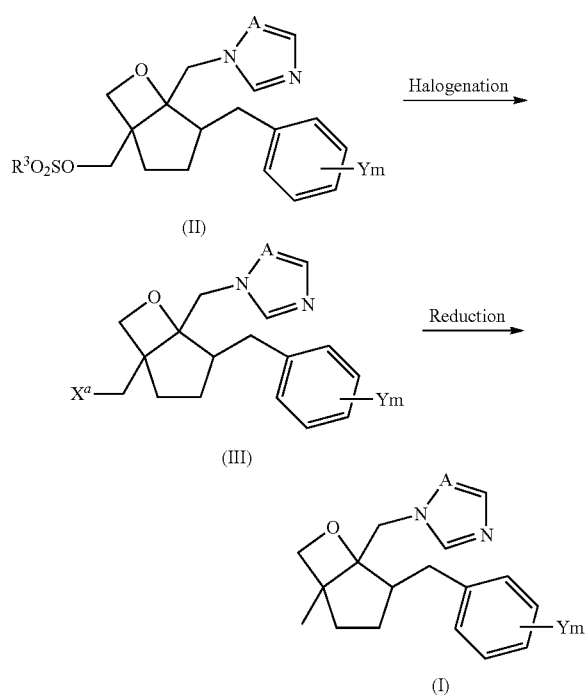

In General Formula (III), Y, m and A are the same as Y, m and A in General Formula (I), respectively, and $X^a$ is the same as the halogen atom in the halogenating agent.

Because the compound represented by General Formula (III) (referred to as Compound (III) below) is unstable like Compound (II), the halogenation of Compound (II) and the reduction of the resulting Compound (III) occurs more rapidly, and a higher yield of Compound (I) can be synthesized. This is why the reduction reaction is performed in the presence of both a halogenating agent and a hydride-based reducing agent in the reaction system of the manufacturing method of the present invention. From the standpoint of improving the yield, it is presumed that the halogenating agent and the hydride-type reducing agent are added to the reaction system at about the same time and that halogenated Compound (III) is somewhat less stable than Compound (II). Therefore, the halogenating agent is preferably added to the reaction system right after the hydride-type reducing agent has been added.

The solvent used in the reaction may be selected based on the combination of halogenating agent and reducing agent that is being used. Examples of solvents include ether-based solvents such as dimethoxyethane, diethyl ether, tetrahydrofuran, methyl tert-butyl ether, 1,4-dioxane and diethylene glycol dimethyl ether; amide-based solvents such as N,N-dimethylacetamide, N-methylpyrrolidone and dimethylpropyleneurea; alcohol-based solvents such as isopropanol and tert-butanol; sulfoxide-based solvents such as dimethyl sulfoxide; hydrocarbon solvents such as pentane, hexane, toluene, benzene and xylene; and halogen-based solvents such as 1,2-dichloroethane, chloroform and chlorobenzene. These solvents can be used alone or in combinations of two or more. Among these, ether-based solvents, amide-base solvents, and mixtures containing these as a component are preferred. Dimethoxyethane, tetrahydrofuran, N,N-dimethylacetamide, and N-methylpyrrolidone are especially preferred.

The amount of halogenating agent used is usually from 0.5 to 10 times, and preferably from 0.8 to 5 times, the amount of Compound (II) in terms of the mole ratio.

The amount of reducing agent used is usually from 0.2 to 20 times, and preferably from 0.3 to 10 times, the amount of Compound (II) in terms of the mole ratio. When the reducing agent is sodium borohydride, the amount is usually from 0.2 to 10 times, and preferably 0.3 to 5 times in terms of the mole ratio.

The reaction temperature depends on the solvent, halogenating agent and reducing agent that are used, but is preferably from −50° C. to 150° C. and more preferably from −10° C. to 100° C. The reaction time depends on the solvent, halogenating agent and reducing agent that are used, but is preferably from 0.1 hours to 3 days and more preferably from 0.5 hours to 2 days.

As explained above, Compound (I) is preferably obtained by adding the halogenating agent and the reducing agent to the reaction solution without isolating Compound (II) from the reaction solution when Compound (II) is obtained by simultaneously producing an oxetane from and sulfonylating a compound represented by General Formula (IV) in the presence of a sulfonyl chloride and base in a solvent. Because Compound (II) is unstable, the concentration step and isolation step can be eliminated and the yield of Compound (I) can be further improved. Examples of solvents that can be used here include ether-based solvents, especially dimethoxyethane and tetrahydrofuran, and amide-based solvents, especially N,N-dimethylacetamide and N-methylpyrrolidone.

The reduction reaction is stopped (quenched) by the supplying of protons. When the proton source is supplied during the reaction, the proton source should be less reactive than Compound (II), Compound (III) and the reducing agent. The proton source can be water, an alcohol, an acid, or any mixture of these. Examples of alcohols include isopropanol and tert-butanol. Examples of acids include inorganic acids such as sulfuric acid and hydrochloric acid, and organic acids such as acetic acid, carbonic acid, formic acid and citric acid.

The amount of proton source added depends on the amount of reducing agent being used. For example, the amount of proton source added is usually from 0.5 to 1000 times, and preferably from 0.8 to 100 times, the amount of reducing agent in terms of the mole ratio. When the reducing agent is sodium borohydride, the amount added is usually from 0.5 to 50 times, and preferably from 1 to 20 times, in terms of the mole ratio. The proton source may be added to the reaction more than once.

Compound (I) obtained from the reaction solution is passed through other manufacturing steps such as an oxetane ring-opening reaction, and used as an active ingredient in agricultural and horticultural agents and in industrial material protecting agents.

EXAMPLES

The following is a detailed explanation of the present invention with reference to examples.

Example 1

Synthesis (I) of 4-(4-chlorobenzyl)-1-methyl-5-(1H-1,2,4-triazol-1-ylmethyl)-6-oxabicyclo[3,2,0]heptane (Compound (3))

The following chemical reactions were performed in the present example.

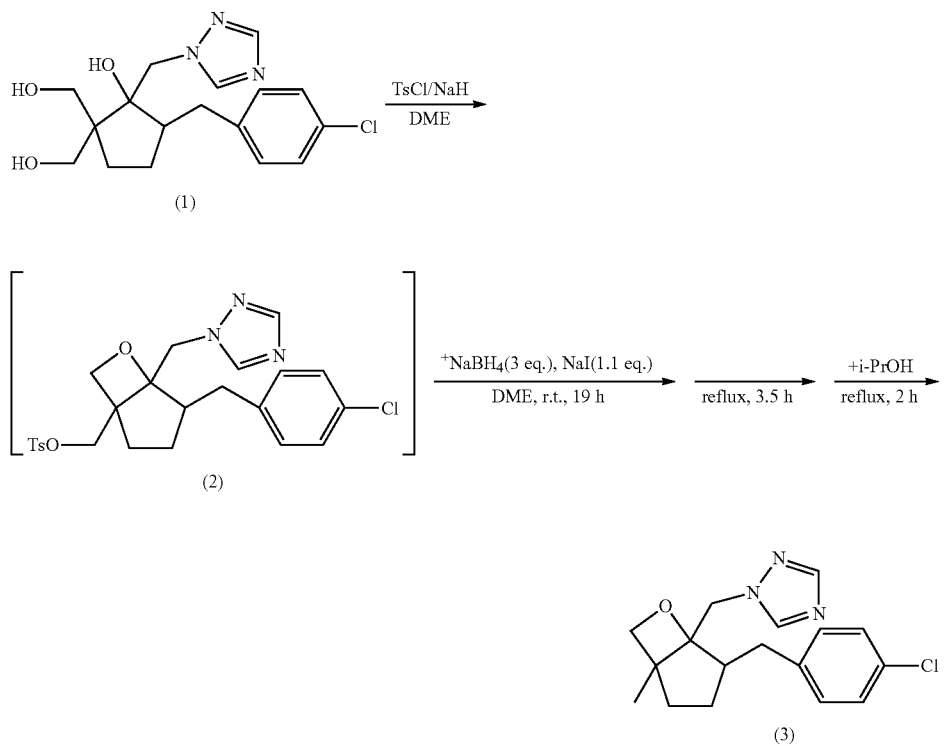

Formula 8

5-(4-chlorobenzyl)-2,2-bis(hydroxymethyl)-1-(1H-1,2,4-triazol-1-yl)cyclopentanol (Compound (1), 0.50 g, 0.00142 mol) was dissolved in 1,2-dimethoxyethane (DME, 15 ml), NaH (0.22 g (ca. 60% in mineral oil), 0.00142×3.9 mol) was added, and the solution was stirred for 10 minutes at room temperature. After ice-cooling the solution, p-toluenesulfonyl chloride (TsCl, 0.677 g, 0.00142×2.5 mol) was added, and the solution was stirred for 0.5 hours at the same temperature. The solution was then removed from the ice bath and stirred for 1 hour. Next, NaBH₄ (0.16 g, 0.00142×3.0 mol) and NaI (0.234 g, 0.00142×1.1 mol) were added, the solution was stirred for 19 hours at room temperature, and then allowed to react under reflux for 3.5 hours. After the reaction, isopropanol (2 ml) was added, the solution allowed to react under reflux for another 2 hours, and then allowed to cool. Acetone (3 ml) was added to the reaction solution and stirred for 20 minutes. Afterwards, 48 wt % sulfuric acid aqueous solution (1 ml) and water (4 ml) were added, and the solution was stirred for approximately 10 minutes. Next, a saturated aqueous solution of sodium bicarbonate was added and then extracted using ethyl acetate. After washing the organic layer using a saturated aqueous solution of sodium chloride, the organic layer was dried using anhydrous sodium sulfate and concentrated. The concentrate was refined using a silica gel column to obtain the target compound (Compound (3)).

Yield (Amount): 0.255 g (0.000802 mol)
Yield (Percentage): 57%
White Solid

Example 2

Synthesis (II) of Compound (3)

The following chemical reactions were performed in the present example.

Formula 9

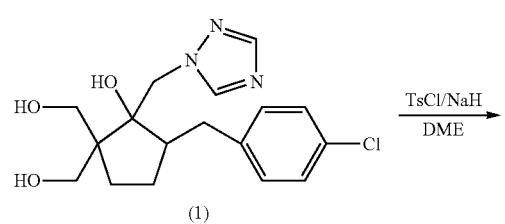

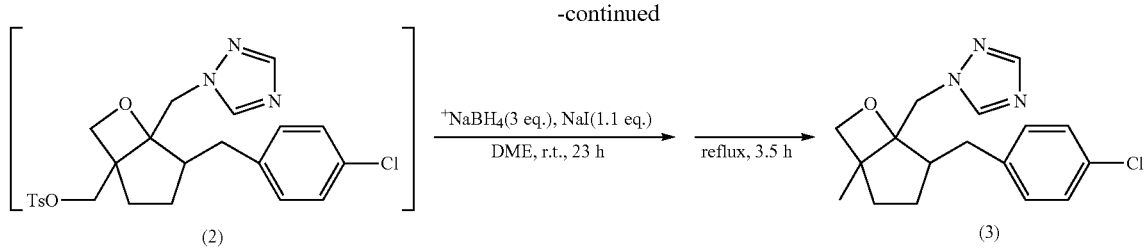

Compound (1) (0.50 g, 0.00142 mol) was dissolved in 1,2-dimethoxyethane (DME, 15 ml), NaH (0.22 g (ca. 60% in mineral oil), 0.00142×3.9 mol) was added, and the solution was stirred for 10 minutes at room temperature. After ice-cooling the solution, p-toluenesulfonyl chloride (TsCl, 0.677 g, 0.00142×2.5 mol) was added, and the solution was stirred for 0.5 hours at the same temperature. The solution was then removed from the ice bath and stirred for 1 hour. Next, NaBH$_4$ (0.16 g, 0.00142×3.0 mol) and NaI (0.234 g, 0.00142×1.1 mol) were added, the solution was stirred for 23 hours at room temperature, and then allowed to react under reflux for 3.5 hours. After the reaction solution had cooled, acetone (3 ml) was added and the solution was stirred for 20 minutes. Afterwards, 48 wt % sulfuric acid aqueous solution (1 ml) and water (4 ml) were added, and the solution was stirred for approximately 10 minutes. Next, a saturated aqueous solution of sodium bicarbonate was added and then extracted using ethyl acetate. After washing the organic layer using a saturated aqueous solution of sodium chloride, the organic layer was dried using anhydrous sodium sulfate and concentrated. The concentrate was refined using a silica gel column to obtain the target compound (Compound (3)).

Yield (Amount): 0.299 g (0.000941 mol)

Yield (Percentage): 66%

White Solid

Example 3

Synthesis (III) of Compound (3)

The following chemical reactions were performed in the present example.

Formula 10

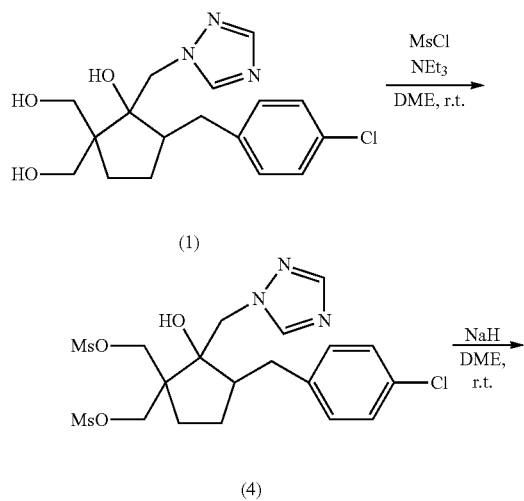

(1) Synthesis of Compound (4)

Compound (1) (0.50 g, 0.00142 mol) and triethyl amine (0.70 ml, 0.00142×3.5 mol) were dissolved in DME (15 ml). After adding mesyl chloride (0.30 ml, 0.00142×2.7 mol) under ice-cooling, the solution was removed from the ice bath and then stirred for 5 hours at room temperature. After stirring, 1N aqueous hydrochloric acid (30 ml) was added to the reaction solution and then extracted using ethyl acetate. After washing the organic layer using a saturated aqueous solution of sodium bicarbonate solution and a saturated aqueous solution of sodium chloride, the organic layer was dried using anhydrous sodium sulfate and then concentrated. The concentrate was refined using a silica gel column to obtain white, viscous [3-(4-chlorobenzyl)-2-hydroxy-1-methylsulfonyloxymethyl-2-(1H-1,2,4-triazol-1-ylmethyl)cyclopentyl]methyl methanesulfonate (Compound (4)).

Yield: 0.688 g (Percentage: 95%)

(2) Synthesis of Compound (3) From Compound (4)

Compound (4) (0.75 g, 0.00148 mol) was dissolved in 1,2-dimethoxyethane (DME, 5 ml), NaH (0.066 g (ca. 60% in mineral oil), 0.00148×1.1 mol) was added, and the solution was stirred for 0.5 hours at room temperature. Next, NaBH$_4$ (0.168 g, 0.00148×3.0 mol) and NaI (0.243 g, 0.00148×1.1 mol) were added, the solution was stirred for 27 hours at room temperature, and then allowed to react for 1 hour at approximately 60° C. After the reaction solution had cooled, 48 wt % sulfuric acid aqueous solution (2 ml) and water (4 ml) were added, and the solution was stirred for approximately 4 hours. After neutralizing the reaction with an aqueous solution of sodium bicarbonate, it was extracted using ethyl acetate. After washing the organic layer using a saturated aqueous solution of sodium chloride, the organic layer was dried using

Example 4

Synthesis (IV) of Compound (3)

The following chemical reactions were performed in the present example.

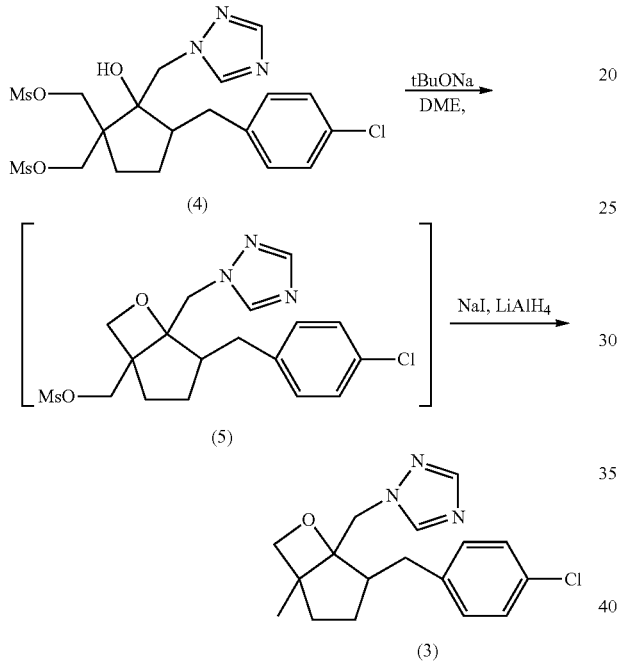

Compound (4) (0.80 g, 0.00157 mol) was dissolved in 1,2-dimethoxyethane (DME, 15 ml) in an argon atmosphere, tBuONa (0.17 g, 0.00157×1.1 mol) was added, and the solution was stirred for 1 hour at room temperature. NaI (0.260 g, 0.00157×1.1 mol) and LiAlH₄ (0.18 g, 0.00157×3.0 mol) were added to the reaction solution, and the solution was stirred for 18 hours at room temperature.

The reaction solution was poured into 25 wt % sulfuric acid aqueous solution (20 ml) to stop the reaction, and then extracted using ethyl acetate. After washing the organic layer using a saturated aqueous solution of sodium bicarbonate solution and a saturated aqueous solution of sodium chloride, the organic layer was dried using anhydrous sodium sulfate and then concentrated. The concentrate was refined using a silica gel column to obtain Compound (3).

Yield (Amount): 0.156 g (0.00049 mol)
Yield (Percentage): 31%
White Solid

INDUSTRIAL APPLICABILITY

The present invention can be applied to the manufacture of 4-benzyl-1-methyl-6-oxabicyclo[3,2,0]heptane derivatives used as a raw material in agrochemicals.

The invention claimed is:

1. A method for manufacturing a compound represented by General Formula (I) below:

Formula 1 in General Formula (I), Y represents a halogen atom, an alkyl group having 1 to 4 carbon atoms, a haloalkyl group having 1 to 4 carbon atoms, an alkoxy group having 1 to 4 carbon atoms, a haloalkoxy group having 1 to 4 carbon atoms, or a phenyl group, m represents an integer from 0 to 5, Y being the same or different when m is an integer equal to or greater than 2, and A represents a nitrogen atom or a methine group;

a compound represented by General Formula (II) below being reduced in the presence of both a halogenating agent and a hydride-type reducing agent;

Formula 2 in General Formula (II), Y, m and A are the same as Y, m and A in General Formula (I), respectively, $R^3$ represents an alkyl group having 1 to 3 carbon atoms, a haloalkyl group having 1 to 3 carbon atoms, a substitutable phenyl group, or a substitutable naphthyl group.

2. The manufacturing method according to claim 1, wherein the halogenating agent is an alkali metal halide.

3. The manufacturing method according to claim 1, wherein the hydride-type reducing agent is a borohydride compound or an aluminum hydride compound.

4. The manufacturing method according to claim 3, wherein the hydride-type reducing agent is sodium borohydride, lithium borohydride, sodium trimethoxyborohydride, lithium aluminum hydride, or sodium bis(2-methoxyethoxy)aluminum hydride.

5. The manufacturing method according to claim 1, wherein the halogenating agent is sodium iodide or potassium iodide, and the hydride-type reducing agent is sodium borohydride.

6. The manufacturing method according to claim 1, wherein m in General Formula (I) above is an integer from 0 to 3, and Y is a halogen atom, an alkyl group having 1 to 3 carbon atoms, a haloalkyl group having 1 to 3 carbon atoms, an alkoxy group having 1 to 3 carbon atoms or a haloalkoxy group having 1 to 3 carbon atoms, and A represents a nitrogen atom when m is equal to or greater than 1.

7. The manufacturing method according to claim 1, wherein m in General Formula (I) above is an integer from 0 to 2, and Y represents a halogen atom and A represents a nitrogen atom when m is equal to or greater than 1.

8. The manufacturing method according to claim 1, wherein $R^3$ in General Formula (II) above represents a methyl group or 4-methylphenyl group.

* * * * *